(12) United States Patent
Heske et al.

(10) Patent No.: US 7,762,961 B2
(45) Date of Patent: Jul. 27, 2010

(54) PRESSURE GENERATING UNIT

(75) Inventors: Norbert Heske, Kottgeisering (DE); Thomas Heske, Grafrath (DE)

(73) Assignee: C. R. Bard, Inc., Murray Hill, NJ (US)

( * ) Notice: Subject to any disclaimer, the term of this patent is extended or adjusted under 35 U.S.C. 154(b) by 1326 days.

(21) Appl. No.: 10/549,818

(22) PCT Filed: Mar. 29, 2004

(86) PCT No.: PCT/EP2004/003328

§ 371 (c)(1), (2), (4) Date: Sep. 20, 2005

(87) PCT Pub. No.: WO2004/086978

PCT Pub. Date: Oct. 14, 2004

(65) Prior Publication Data

US 2006/0293610 A1    Dec. 28, 2006

(30) Foreign Application Priority Data

Mar. 29, 2003 (DE) ................. 103 14 240

(51) Int. Cl.
*A61B 10/00* (2006.01)
*A61B 5/00* (2006.01)
*B65D 81/00* (2006.01)

(52) U.S. Cl. .............. 600/567; 600/562; 600/563; 600/564; 600/565; 600/566; 600/568; 600/569; 600/570; 600/571; 600/572; 600/573

(58) Field of Classification Search ............. 600/567, 600/571, 565, 562, 563, 564, 566, 568, 569, 600/570, 572, 573
See application file for complete search history.

(56) References Cited

U.S. PATENT DOCUMENTS

| 3,224,434 A | 12/1965 | Molomut et al. |
| 3,565,074 A | 2/1971 | Foti et al. |
| 3,606,878 A | 9/1971 | Kellogg, Jr. |
| 3,844,272 A | 10/1974 | Banko |

(Continued)

FOREIGN PATENT DOCUMENTS

DE    202 04 363    *  7/2002

(Continued)

OTHER PUBLICATIONS

Intn'l. Prelim. Report, Feb. 22, 2006, PCT/EP2004/003328.
Intn'l. Search Report, Nov. 8, 2004, PCT/EP2004/003328.

*Primary Examiner*—Max Hindenburg
*Assistant Examiner*—Jeffrey G Hoekstra

(57) ABSTRACT

The invention relates to pressure generating units, in particular to pressure generating unit arranged in the hand piece of a vacuum biopsy device in the form of a sirynge (2). In said units, air intake is open by a piston when said piston (5) is in the rear position thereof in the space of a vacuumed cylinder (11) which is switched for generating a superpressure, thereby initiating the outflow of a tissue liquid by the air introduced into the space of the vacuumed cylinder. For this purpose, the space of the vacuumed cylinder is connected to the space of an atmosphere pressure cylinder (12) arranged behind the piston, by means of a connection line (15), and an absorbing element (14) is placed on the piston axis.

18 Claims, 2 Drawing Sheets

U.S. PATENT DOCUMENTS

Figure 1:
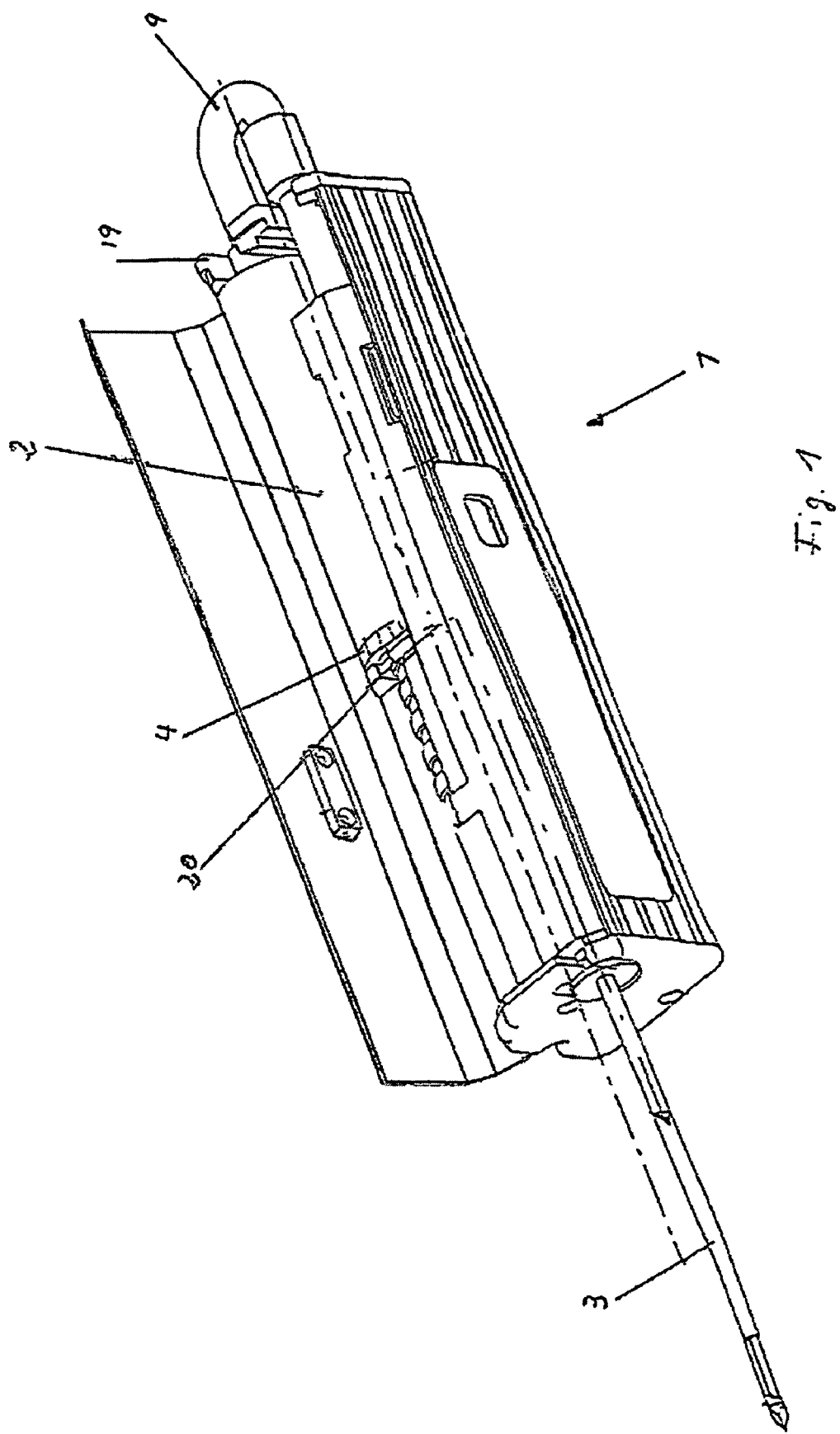

| | | | |
|---|---|---|---|
| 4,275,730 A | 6/1981 | Hussein | |
| 4,490,137 A | 12/1984 | Moukheibir | |
| 4,549,554 A | 10/1985 | Markham | |
| RE33,258 E | 7/1990 | Onik et al. | |
| 4,940,061 A | 7/1990 | Terwilliger et al. | |
| 4,958,625 A | 9/1990 | Bates et al. | |
| 4,967,762 A | 11/1990 | DeVries | |
| 5,025,797 A | 6/1991 | Baran | |
| 5,125,413 A | 6/1992 | Baran | |
| 5,282,476 A | 2/1994 | Terwilliger | |
| 5,368,029 A * | 11/1994 | Holcombe et al. | 600/368 |
| 5,368,045 A | 11/1994 | Bates et al. | |
| 5,400,798 A | 3/1995 | Baran | |
| 5,526,822 A | 6/1996 | Burbank et al. | |
| 5,546,957 A | 8/1996 | Heske | |
| 5,601,585 A | 2/1997 | Banik et al. | |
| 5,617,874 A | 4/1997 | Baran | |
| 5,649,547 A | 7/1997 | Ritchart et al. | |
| 5,655,542 A | 8/1997 | Weilandt | |
| 5,709,697 A | 1/1998 | Ratcliff et al. | |
| 5,752,923 A | 5/1998 | Terwilliger | |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A | 7/1998 | Burbank et al. | |
| 5,788,651 A | 8/1998 | Weilandt | |
| 5,807,282 A | 9/1998 | Fowler | |
| 5,817,033 A | 10/1998 | DeSantis et al. | |
| 5,817,034 A | 10/1998 | Milliman et al. | |
| 5,823,970 A | 10/1998 | Terwilliger | |
| 5,830,219 A | 11/1998 | Bird et al. | |
| D403,405 S | 12/1998 | Terwilliger | |
| 5,857,982 A | 1/1999 | Milliman et al. | |
| 5,913,857 A | 6/1999 | Ritchart et al. | |
| 5,928,164 A | 7/1999 | Burbank et al. | |
| 5,944,673 A | 8/1999 | Gregoire et al. | |
| 5,951,490 A | 9/1999 | Fowler | |
| 5,964,716 A | 10/1999 | Gregoire et al. | |
| 5,971,939 A | 10/1999 | DeSantis et al. | |
| 5,976,164 A | 11/1999 | Mueller et al. | |
| 5,980,469 A | 11/1999 | Burbank et al. | |
| 6,007,495 A | 12/1999 | Matula | |
| 6,007,497 A | 12/1999 | Huitema | |
| 6,017,316 A | 1/2000 | Ritchart et al. | |
| 6,019,733 A | 2/2000 | Farascioni | |
| 6,022,324 A | 2/2000 | Skinner | |
| 6,027,458 A | 2/2000 | Janssens | |
| 6,036,657 A | 3/2000 | Milliman et al. | |
| 6,050,955 A | 4/2000 | Bryan et al. | |
| 6,077,230 A | 6/2000 | Gregoire et al. | |
| 6,083,176 A | 7/2000 | Terwilliger | |
| 6,083,237 A | 7/2000 | Huitema et al. | |
| 6,086,544 A | 7/2000 | Hibner et al. | |
| 6,106,484 A | 8/2000 | Terwilliger | |
| 6,110,129 A | 8/2000 | Terwilliger | |
| 6,120,462 A | 9/2000 | Hibner et al. | |
| 6,126,617 A | 10/2000 | Weilandt et al. | |
| 6,142,955 A | 11/2000 | Farascioni et al. | |
| 6,162,187 A | 12/2000 | Buzzard et al. | |
| 6,165,136 A | 12/2000 | Nishtala | |
| 6,193,673 B1 | 2/2001 | Viola et al. | |
| 6,196,978 B1 | 3/2001 | Weilandt et al. | |
| 6,213,957 B1 | 4/2001 | Milliman et al. | |
| 6,231,522 B1 | 5/2001 | Voegele et al. | |
| 6,241,687 B1 | 6/2001 | Voegele et al. | |
| 6,273,861 B1 | 8/2001 | Bates et al. | |
| 6,273,862 B1 | 8/2001 | Privitera et al. | |
| 6,280,398 B1 | 8/2001 | Ritchart et al. | |
| 6,283,925 B1 | 9/2001 | Terwilliger | |
| 6,322,523 B2 | 11/2001 | Weilandt et al. | |
| 6,328,701 B1 | 12/2001 | Terwilliger | |
| 6,331,166 B1 | 12/2001 | Burbank et al. | |
| 6,402,701 B1 | 6/2002 | Kaplan et al. | |
| 6,428,486 B2 | 8/2002 | Ritchart et al. | |
| 6,428,487 B1 | 8/2002 | Burdorff et al. | |
| 6,432,064 B1 | 8/2002 | Hibner et al. | |
| 6,432,065 B1 | 8/2002 | Burdoff et al. | |
| 6,436,054 B1 | 8/2002 | Viola et al. | |
| 6,488,636 B2 | 12/2002 | Bryan et al. | |
| 6,540,694 B1 | 4/2003 | Van Bladel et al. | |
| 6,540,761 B2 | 4/2003 | Houser | |
| 6,551,255 B2 | 4/2003 | Van Bladel et al. | |
| 6,554,779 B2 | 4/2003 | Viola et al. | |
| 6,585,664 B2 | 7/2003 | Burdoff et al. | |
| 6,638,235 B2 | 10/2003 | Miller et al. | |
| 6,659,105 B2 | 12/2003 | Burbank et al. | |
| 6,689,072 B2 | 2/2004 | Kaplan et al. | |
| 6,752,768 B2 | 6/2004 | Burdoff et al. | |
| 6,758,824 B1 | 7/2004 | Miller et al. | |
| 6,764,495 B2 | 7/2004 | Lee et al. | |
| 6,849,080 B2 | 2/2005 | Lee et al. | |
| 7,153,274 B2 | 12/2006 | Stephens et al. | |
| 7,189,206 B2 | 3/2007 | Quick et al. | |
| 7,226,424 B2 | 6/2007 | Ritchart et al. | |
| 7,347,829 B2 | 3/2008 | Mark et al. | |
| 7,452,367 B2 | 11/2008 | Rassman et al. | |
| 7,648,466 B2 | 1/2010 | Stephens et al. | |
| 2001/0007925 A1 | 7/2001 | Ritchart et al. | |
| 2001/0011156 A1 | 8/2001 | Viola et al. | |
| 2001/0012919 A1 | 8/2001 | Terwilliger | |
| 2001/0014779 A1 | 8/2001 | Lubock et al. | |
| 2001/0047183 A1 | 11/2001 | Privitera et al. | |
| 2002/0016555 A1 | 2/2002 | Ritchart et al. | |
| 2002/0045840 A1 | 4/2002 | Voegele et al. | |
| 2002/0045842 A1 | 4/2002 | Van Bladel et al. | |
| 2002/0068878 A1 | 6/2002 | Jassoni et al. | |
| 2002/0082518 A1 | 6/2002 | Weiss et al. | |
| 2002/0082519 A1 | 6/2002 | Miller et al. | |
| 2002/0120212 A1 | 8/2002 | Ritchart et al. | |
| 2002/0151822 A1 | 10/2002 | Burdoff et al. | |
| 2002/0156395 A1 | 10/2002 | Stephens et al. | |
| 2004/0186393 A1 | 9/2004 | Leigh et al. | |
| 2004/0215103 A1 | 10/2004 | Mueller, Jr. et al. | |
| 2004/0249278 A1 | 12/2004 | Krause | |
| 2004/0249307 A1 | 12/2004 | Thompson et al. | |
| 2005/0004492 A1 | 1/2005 | Burbank et al. | |
| 2005/0010131 A1 | 1/2005 | Burbank et al. | |
| 2005/0027210 A1 | 2/2005 | Miller | |
| 2005/0049521 A1 | 3/2005 | Miller et al. | |
| 2005/0165328 A1 | 7/2005 | Heske et al. | |
| 2005/0203439 A1* | 9/2005 | Heske et al. | 600/566 |
| 2006/0173377 A1 | 8/2006 | McCullough et al. | |
| 2007/0027407 A1 | 2/2007 | Miller | |
| 2007/0032741 A1 | 2/2007 | Hibner et al. | |
| 2007/0106176 A1 | 5/2007 | Mark et al. | |
| 2007/0149894 A1 | 6/2007 | Heske et al. | |
| 2007/0149895 A1 | 6/2007 | McCullough et al. | |
| 2007/0270710 A1 | 11/2007 | Frass et al. | |
| 2008/0154151 A1 | 6/2008 | Ritchart et al. | |

FOREIGN PATENT DOCUMENTS

| | | |
|---|---|---|
| EP | 0890339 | 1/1999 |
| EP | 0995400 A1 | 4/2000 |
| EP | 1 074 271 A2 | 2/2001 |
| EP | 1074271 | 2/2001 |
| GB | 2018601 | 10/1979 |
| WO | WO 96/28097 | 9/1996 |

| WO | WO 98/25522 | 6/1998 |
| WO | WO 00/30546 | 6/2000 |
| WO | WO 00/59378 | 10/2000 |
| WO | WO 02/32318 A1 | 4/2002 |
| WO | WO 02/069808 A2 | 9/2002 |

* cited by examiner

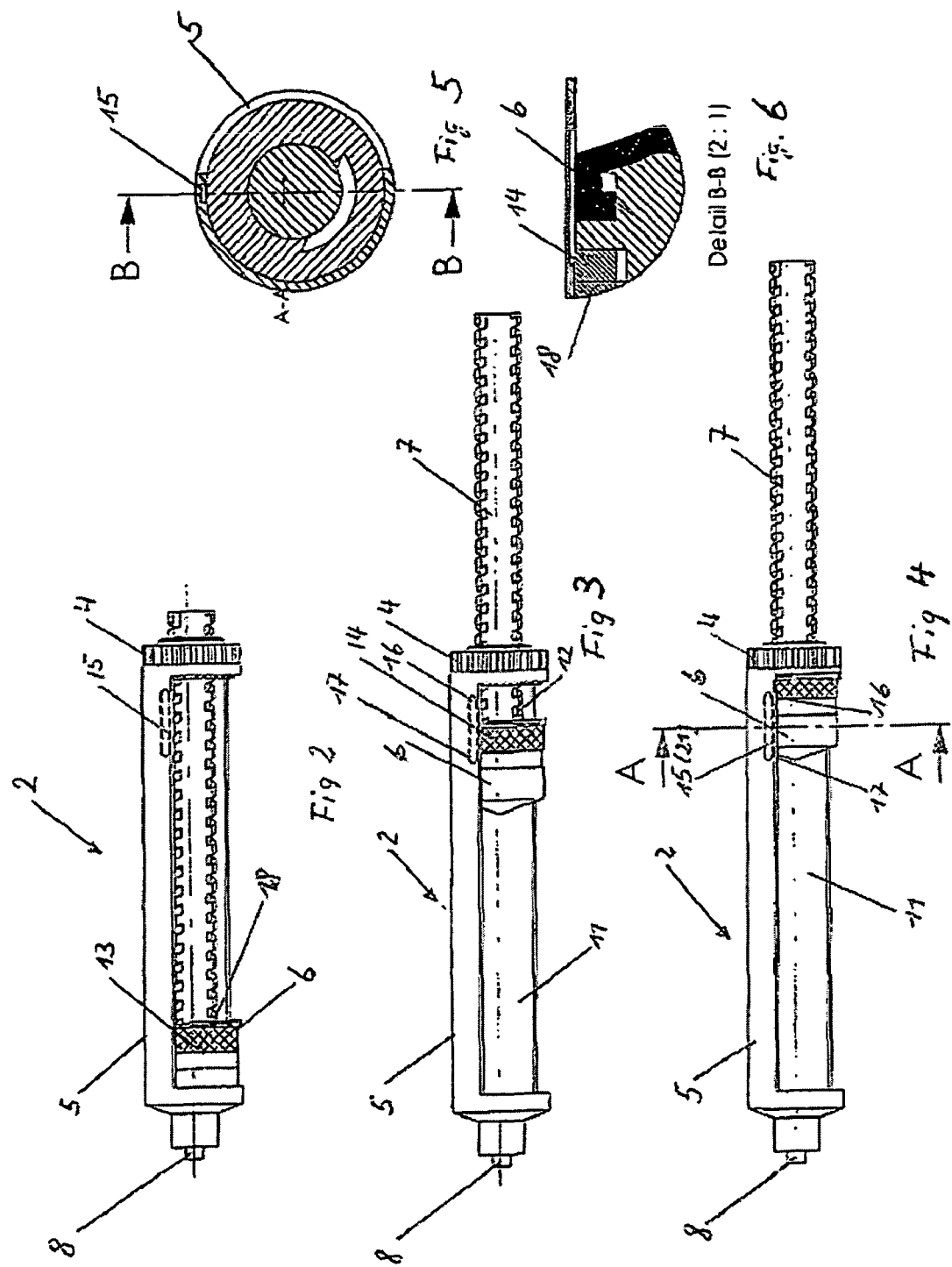

PRESSURE GENERATING UNIT

The invention relates to a pressure generating unit, in particular a pressure generating unit that is arranged in the handpiece of a vacuum biopsy apparatus that is embodied as a type of syringe and whereby, by retracting the piston in the evacuated cylinder space when changing over to generating overpressure, the air supply is released by the position of the piston.

Such a pressure generating unit in a vacuum biopsy apparatus is known from GMS 202 04363or GMS 20211934. The pressure generating unit is connected via a connecting line to a biopsy needle unit that is inserted into the tissue to be examined. The pressure generating unit and the needle unit are arranged parallel in the housing of a handpiece. A vacuum is generated in the needle space for removing the specimen by means of the pressure generating unit.

In order to be able to use the pressure generating unit for generating an overpressure as well, an aeration aperture is provided, and when it is released by the syringe piston, the vacuum that was generated is removed so that the air that has since penetrated can be compressed by means of the syringe piston.

Because not only the specimen is drawn into the specimen removal space by the vacuum, but also tissue fluid is drawn in, when the aeration aperture is briefly released, tissue fluid that has penetrated into the cylinder piston space can flow out into the interior of the handpiece, in particular when the pressure generating unit and/or the handpiece with the needle unit and the pressure generating unit connected thereto is in an unfavorable position. In order to prevent this, it has already been suggested to seal the aeration aperture by means of a sponge that is arranged on the exterior of the piston cylinder. However, this is not sufficient in all cases.

The object of the invention is, therefore, first to allow the air required for removing the vacuum to flow into the cylinder and, second, to reliably prevent outflowing tissue fluid from contaminating the housing interior space of the handpiece.

This object is obtained by connecting the evacuated cylinder space is connected via a connecting line to the cylinder space that is under atmospheric pressure and is on the other piston side, and by providing an absorbent element on the piston spindle.

By arranging a connection between the two cylinder spaces that are divided by the piston, whereby the connection is released or closed by the position of the piston, and by arranging an absorbent element in the cylinder space that is under atmospheric pressure, on the one hand air can flow into the evacuated part of the cylinder from outside, and on the other hand outflowing tissue fluid is drawn out of the evacuated cylinder part by the absorbent element. The length of the connection is selected so that the groove after the release of the connection for the inflow of air, the aperture of the cylinder space ending under atmospheric pressure, is over the absorbent element [sic]. This has the advantage that any tissue fluid that escapes during the brief opening of the connection is conducted directly into the element and absorbed by it.

The use of an air-permeable absorbent element furthermore has the advantage that the air coming in is filtered and thus particles cannot enter into the cylinder space.

It has proved particularly simple and cost-effective to use chemical pulp, in particular absorbent paper, as the material for the element.

It is advantageous that the element is held so that it cannot be displaced by means of a securing disk arranged on the piston spindle. This has the advantage that the element cannot migrate on the piston spindle during operation, which reduces the effectiveness of the element.

The invention is explained in greater detail below by means of an exemplary embodiment:

FIG. 1: The biopsy apparatus

FIG. 2: The pressure generating unit with piston pushed in (partial cut-away)

FIG. 3: The pressure generating unit after generating a vacuum by retracting the piston FIG. 4: The pressure generating unit after releasing the connection for aeration FIG. 5: Section A-A through FIG. 4

FIG. 6: Section B-B through FIG. 5

FIG. 1 illustrates a biopsy apparatus 1 in which the pressure generating unit 2 is housed in a housing with a needle unit 3 that is situated parallel thereto. The pressure generating unit is driven, for example, via an electro-gear motor (not shown) via the toothed wheel 4.

The pressure generating unit 2, which is constructed as a type of syringe, comprises a cylinder 5 in which a piston 6 is longitudinally displaceable by means of a piston spindle 7. The piston spindle drive comprises a toothed wheel 4 mounted on the open end of the cylinder, whereby the center of the toothed wheel is embodied as a spindle nut that interacts with the piston spindle 7 mounted therein. The piston spindle 7 is moved to the connector 8 or to the toothed wheel 4 by means of the toothed wheel 4, depending on the direction of rotation of the motor, via a pinion (not shown) that sits on the shaft of an electromotor. The cylinder of the pressure generating unit has at one end a connector 8 for a connecting piece 9 that is connected to the biopsy needle unit 3. Arranged on the side opposite the connector is a toothed wheel 4 with an interior spindle thread (spindle nut) that interacts with the piston spindle 7 so that with each rotation of the toothed wheel the piston 6 travels a precisely defined path to the one or the other side, depending on motor rotation. The toothed wheel can be mounted in the open cylinder end.

Depending on the direction of rotation, the piston 3 can be moved via the toothed wheel/spindle drive to the cylinder floor or away from the cylinder floor to the toothed wheel. The pressure generating unit is fitted for instance in a biopsy apparatus as it is illustrated in FIG. 1 and as it is described in greater detail in GMS 202 04 363; the distance between the housing wall 19 and insertion groove 20 for the piston spindle is selected so that the pressure generating unit cannot move in the longitudinal axis and the toothed wheel 4 is thus supported in the cylinder. When the piston is retracted to just in front of the aperture for the connecting line 21, here a groove 15 in the cylinder wall, i.e., in the direction of the toothed wheel 4, a vacuum forms in the biopsy needle system (see FIG. 3). After the air supply is released in the cylinder space 11 (opening of connecting line, groove is opened)—as described in the following—the underpressure previously created in the biopsy needle system (see FIG. 4) is removed by the inflow of air. If the piston is moved in the direction of the connector 8 after the air has flowed in, overpressure is created in the system.

The piston spindle carries the piston 10 with a rubber jacket on the side opposite the drive, i.e., on the connector side. On the interior piston cylinder wall, the rubber jacket of the piston seals the left-hand cylinder space 11 (space in front of the connector) from the cylinder space 12. In other words, if the connector support 8 is connected to the biopsy needle unit via the connecting piece 9 and the biopsy needle is inserted into tissue, for example, an underpressure occurs in the biopsy needle system due to the displacement of the piston to the drive side. The cylinder space 12 is furthermore under atmospheric pressure. Arranged on the side wall 13 of the piston, which is in the cylinder space 12, is an absorbent element 14 that is penetrated coaxially by the piston spindle and that is held, for example by means of a securing disk 18 that is attached to the piston spindle. The element is round and is situated so that it acts as a minor seal against the interior cylinder wall of the cylinder. In order to make it easy to pass over the piston spindle, the element embodied as a punched disk is slit. The element can comprise a plurality of individual disks that are approx. 1 mm thick. It can also be a single part, however. It extends approx. 3 mm. The element is placed directly on the piston side wall 13 and is held by the securing disk. A groove 15 is worked into the interior wall of the cylinder wall as a connection 21 on the cylinder part adjacent to the toothed wheel 4. As FIG. 5 illustrates, the depth of the groove is approximately half the wall thickness. The groove length (FIG. 5) is selected so that the groove ends when the air supply is released to the center of the absorbent element 14 and the cylinder space 11 to be aerated is connected to the exterior atmospheric pressure via the groove. In this position the groove has to a certain extent two "apertures." The one "aperture 17" ends in the cylinder space 11; the other "aperture 16" ends above the element 14 when the piston is brought to the open position (see FIG. 4).

When employing the vacuum biopsy equipment in accordance with GMS 202 04 363 or 202 11 934, it has been demonstrated that the suction action of the pressure generating unit 2 is so strong that, depending on the position of the biopsy apparatus when the specimen is drawn, more or less tissue fluid can enter into the pressure generating unit 2. By arranging a groove 15 in the interior of the cylinder, which [groove] is primarily needed because of the removal of the underpressure, it is not always possible to avoid the outflow of tissue fluid during the brief opening of the aeration aperture and its subsequent closing.

However, because the groove is designed so that the "aperture 16" ends over the absorbent element, the tissue fluid is absorbed and no tissue fluid flows into the housing of the biopsy handpiece. When the "aperture 16" of the groove is released (see FIG. 4) the air can travel from the cylinder space 9 to the absorbent element via the groove into the cylinder space 11 and remove the vacuum there. In other words, the air is filtered prior to its entering the cylinder space 11. Due to the electronic components installed [there], it is absolutely necessary to prevent the flow of tissue fluid into the housing of the handpiece of the biopsy apparatus because wet cleaning of the handpiece can lead to serious damage to the electronics.

In the exemplary embodiment, an interior groove is provided as a connection from the cylinder space 11 to the cylinder space 12. The connection can also be embodied as an exterior line or as a line that is integrated into the cylinder jacket. What is important for solving the problem is that the tissue fluid that can escape when the vacuum is removed can be intentionally conducted so that the tissue fluid is absorbed by means of an absorbent element and does not enter into the housing.

LIST OF PARTS

1) Biopsy apparatus
2) Pressure generating unit
3) Needle unit
4) Toothed wheel
5) Cylinder
6) Piston
7) Piston spindle
8) Connector
9) Connection piece
10)
11) Cylinder space
12) Cylinder space
13) Side wall
14) Absorbent element
15) Groove
16) Aperture
17) Aperture
18) Securing disk
19) Housing wall
20) Insertion groove
21) Connection line
22)
23)
24)
25)
26)
27)
28)
39)

The invention claimed is:

1. A pressure generating unit for a biopsy apparatus carrying a biopsy needle unit, comprising:
a cylinder having an interior cylinder wall, a first cylinder space, a second cylinder space, a connector, and a connecting path, the connector being located at a first end of the cylinder adjacent the first cylinder space and configured for connection to the biopsy needle unit, the connecting path being configured to facilitate selective connection between the first cylinder space and the second cylinder space;
a piston arrangement including a piston connected to a piston spindle, the piston being movably positioned in the cylinder, a vacuum being generated in the first cylinder space by retracting the piston and the vacuum being released when the piston is positioned adjacent the connecting path; and
an absorbent element carried by the piston, the absorbent element being located in contact against the interior cylinder wall,
wherein the piston separates the first cylinder space from the second cylinder space, and the absorbent element filters air prior to entry into the first cylinder space via the connecting path when the piston is positioned over the connecting path to release the vacuum.

2. The pressure generating unit of claim 1, wherein the absorbent element is arranged on a back side of the piston that faces away from the first end of the cylinder, the absorbent element being held in position by a securing disk attached to the piston spindle.

3. The pressure generating unit of claim 1, further comprising a piston spindle drive engaged with the piston spindle to displace the piston in the cylinder, the piston spindle drive being mounted at a second end of the cylinder opposite to the first end of the cylinder having the connector, the absorbent element being located between a back side of the piston and the piston spindle drive.

4. The pressure generating unit of claim 1, wherein the absorbent element comprises absorbent chemical pulp.

5. The pressure generating unit of claim 1, wherein the absorbent element is a paper filter.

6. The pressure generating unit of claim 1, wherein the absorbent element is an air-permeable element.

7. The pressure generating unit of claim 1, wherein the absorbent element includes a plurality of absorbent disks.

8. The pressure generating unit of claim 1, wherein a longitudinal extent of the absorbent element in the cylinder is about three millimeters.

9. The pressure generating unit of claim 1, wherein the absorbent element is arranged on a back side of the piston that faces away from the first end of the cylinder, and wherein the absorbent element absorbs tissue fluids to prevent a back flow of the tissue fluids from the first cylinder space.

10. A pressure generating unit for a biopsy apparatus carrying a biopsy needle unit, comprising:
 a cylinder having an interior cylinder wall, a first cylinder space, a second cylinder space, a connector, and a connecting path, the connector being located at a first end of the cylinder adjacent the first cylinder space and configured for connection to the biopsy needle unit, the connecting path being configured to facilitate selective connection between the first cylinder space and the second cylinder space;
 a piston arrangement including a piston connected to a piston spindle, the piston being movably positioned in the cylinder, a vacuum being generated in the first cylinder space by retracting the piston and the vacuum being released when the piston is positioned adjacent the connecting path; and
 an absorbent element carried by the piston, the absorbent element being located in contact against the interior cylinder wall,
 wherein the connecting path is an interior groove in the cylinder, and the vacuum is released when the piston and the absorbent element are positioned at the interior groove.

11. The pressure generating unit of claim 10, wherein the absorbent element is arranged on a back side of the piston that faces away from the first end of the cylinder, the absorbent element being held in position by a securing disk attached to the piston spindle.

12. The pressure generating unit of claim 10, further comprising a piston spindle drive engaged with the piston spindle to displace the piston in the cylinder, the piston spindle drive being mounted at a second end of the cylinder opposite to the first end of the cylinder having the connector, the absorbent element being located between a back side of the piston and the piston spindle drive.

13. The pressure generating unit of claim 10, wherein the absorbent element comprises absorbent chemical pulp.

14. The pressure generating unit of claim 10, wherein the absorbent element is a paper filter.

15. The pressure generating unit of claim 10, wherein the absorbent element is an air-permeable element.

16. The pressure generating unit of claim 10, wherein the absorbent element includes a plurality of absorbent disks.

17. The pressure generating unit of claim 10, wherein a longitudinal extent of the absorbent element in the cylinder is about three millimeters.

18. The pressure generating unit of claim 10, wherein the absorbent element is arranged on a back side of the piston that faces away from the first end of the cylinder, and wherein the absorbent element absorbs tissue fluids to prevent a back flow of the tissue fluids from the first cylinder space.

* * * * *